(12) United States Patent
Lu

(10) Patent No.: US 11,756,209 B2
(45) Date of Patent: Sep. 12, 2023

(54) METHOD AND APPARATUS FOR AUTOMATED TARGET AND TISSUE SEGMENTATION USING MULTI-MODAL IMAGING AND ENSEMBLE MACHINE LEARNING MODELS

(71) Applicant: Vysioneer INC., Cambridge, MA (US)

(72) Inventor: Jen-Tang Lu, Cambridge, MA (US)

(73) Assignee: Vysioneer INC., Cambridge, MA (US)

( * ) Notice: Subject to any disclaimer, the term of this patent is extended or adjusted under 35 U.S.C. 154(b) by 0 days.

(21) Appl. No.: 17/373,036

(22) Filed: Jul. 12, 2021

(65) Prior Publication Data
US 2021/0343023 A1 Nov. 4, 2021

Related U.S. Application Data

(63) Continuation of application No. 16/780,144, filed on Feb. 3, 2020, now Pat. No. 11,062,459.
(Continued)

(51) Int. Cl.
*G06K 9/00* (2022.01)
*G06T 7/174* (2017.01)
(Continued)

(52) U.S. Cl.
CPC ............. *G06T 7/174* (2017.01); *G06N 20/20* (2019.01); *G06T 7/0012* (2013.01); *G16H 30/20* (2018.01);
(Continued)

(58) Field of Classification Search
CPC ................... G06T 7/174; G06T 7/0012; G06T 2207/20081; G06T 2207/20221;
(Continued)

(56) References Cited

U.S. PATENT DOCUMENTS

| 2016/0217570 A1* | 7/2016 | Schadewaldt | ........... G06T 7/149 |
| 2017/0014108 A1* | 1/2017 | Mazurowski | ......... G06T 7/0012 |

(Continued)

FOREIGN PATENT DOCUMENTS

| CN | 106682435 A | 5/2017 |
| CN | 109166105 A | 1/2019 |
| TW | 201903708 A | 1/2019 |

OTHER PUBLICATIONS

Nie, et al., "Fully Convolutional Networks for Multi-Modality Isointense Infant Brain Image Segmentation", 2016 IEEE 13th International Symposium on Biomedical Imaging (ISBI) Apr. 1, 2016, pp. 1342-1345.

(Continued)

*Primary Examiner* — Xin Jia
(74) *Attorney, Agent, or Firm* — MOSER TABOADA

(57) ABSTRACT

Methods and systems for automated target and tissue segmentation using multi-modal imaging and ensemble machine learning models are provided herein. In some embodiments, a method comprises: receiving a plurality of medical images, wherein each of the plurality of medical images includes a target and normal tissue; combining the plurality of medical images to align the target and normal tissue across the plurality of medical images; inputting the combined medical images into each of a plurality of machine learning models; receiving, in response to the input, an output from each of the plurality of machine learning models; combining the results of the plurality of machine learning models; generating a final segmentation image based on the combined results of the plurality of machine learning models; assigning a score to each segmented target and normal tissue; and sorting the segmented targets and normal tissues based on the scores.

19 Claims, 6 Drawing Sheets

Related U.S. Application Data

(60) Provisional application No. 62/881,573, filed on Aug. 1, 2019, provisional application No. 62/802,306, filed on Feb. 7, 2019.

(51) Int. Cl.
  *G06N 20/20* (2019.01)
  *G16H 30/40* (2018.01)
  *G06T 7/00* (2017.01)
  *G16H 30/20* (2018.01)

(52) U.S. Cl.
  CPC ... *G16H 30/40* (2018.01); *G06T 2207/20081* (2013.01); *G06T 2207/20221* (2013.01)

(58) Field of Classification Search
  CPC . G06T 2207/30004; G06T 7/11; G06N 20/20; G06N 3/0454; G06N 3/084; G16H 30/20; G16H 30/40; G16H 50/30
  See application file for complete search history.

(56) References Cited

U.S. PATENT DOCUMENTS

| | | | |
|---|---|---|---|
| 2017/0091951 A1* | 3/2017 | Yoo | G06T 7/143 |
| 2018/0061059 A1 | 3/2018 | Xu et al. | |
| 2019/0251694 A1* | 8/2019 | Han | G06T 7/11 |
| 2019/0318474 A1* | 10/2019 | Han | G06V 10/764 |

OTHER PUBLICATIONS

Suk, et al., "Deep Learning-Based Feature Representation for AD/MCI Classification" Sep. 22, 2013, SAT 2015, 18th International Conference, Austin, TX, USA, Sep. 24-27, 2015, pp. 583-590.

Zhang, et al., "Multi-modal multi-task learning for joint prediction of multiple regression and classification variables in Alzheimer's disease", Neuroimage, Elsevier, Amsterdam, NL, vol. 59, No. 2, Sep. 27, 2011, pp. 895-907.

Lyksborg, et al., "An Ensemble of 2D Convolutional Neural Networks for Tumor Segmentation", Jun. 9, 2015, Advances in Databases and Information Systems, Springer International Publishing, pp. 201-211.

Zhou, et al., "A review: Deep learning for medical image segmentation using multi-modality fusion", Arxiv.org, Cornell University Library, Jul. 16, 2020.

European Search Report for Application No. 20752853.0, dated Sep. 29, 2022.

Taiwan Office Action for Application No. 109103841 dated Jun. 8, 2023.

* cited by examiner

METHOD AND APPARATUS FOR AUTOMATED TARGET AND TISSUE SEGMENTATION USING MULTI-MODAL IMAGING AND ENSEMBLE MACHINE LEARNING MODELS

CROSS-REFERENCE TO RELATED APPLICATIONS

This application is a continuation of U.S. patent application Ser. No. 16/780,144 filed Feb. 3, 2020, which claims priority to U.S. Provisional Patent Application Ser. No. 62/802,306 filed Feb. 7, 2019 and U.S. Provisional Patent Application Ser. No. 62/881,573 filed Aug. 1, 2019, both of which are incorporated by reference herein in their entirety.

BACKGROUND

Field

Embodiments consistent with the present invention generally relate to tissue segmentation, and more specifically to a method and apparatus for automated target and tissue segmentation using multi-modal imaging and ensemble machine learning models.

Description of the Related Art

More than half of all cancer patients receive radiotherapy as it delivers high doses of irradiation to eliminate targets, such as tumors, while minimizing the amount of normal tissue irradiated at high radiation doses. Current radiation treatment depends on manually intensive analysis of medical images (such as CT and MR images) in order to delineate tumors and normal healthy organs.

An expert radiation oncologist may spend four hours or more on a single case, causing significant delays to treatment commencement. Also, the high inter-practitioner variability in treatment planning process leads to suboptimal clinical outcomes and unnecessary radiation toxicity.

Therefore, a need exists for automated target and tissue segmentation using multi-modal imaging and ensemble machine learning models.

SUMMARY

A method and system for automated target and tissue segmentation using multi-modal imaging and ensemble machine learning models is provided.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other and further embodiments of the present invention are described below.

BRIEF DESCRIPTION OF THE DRAWINGS

So that the manner in which the above recited features and embodiments of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

Figure 1:
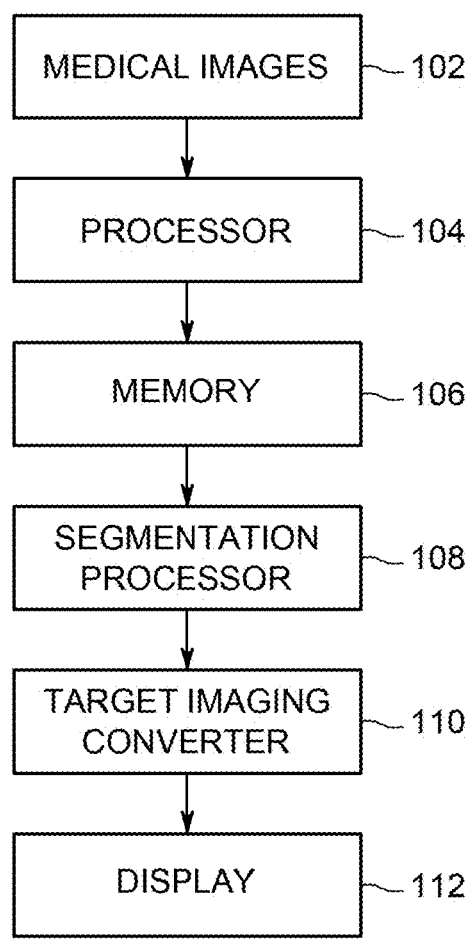
FIG. 1 depicts a block diagram of a system for automated target and tissue segmentation using multi-modal imaging and ensemble machine learning models, configured in accordance with one or more embodiments consistent with the present disclosure.

To facilitate understanding, identical reference numerals have been used where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Embodiments of the present invention include a method and apparatus for automated target and tissue segmentation using multi-modal imaging and ensemble machine learning models. The system provides automated target (e.g., tumor) and normal tissue and/or organ segmentation on medical images for radiotherapy using a plurality of imaging modalities (e.g., computer tomography (CT), magnetic resonance imaging (MRI), positron emission tomography (PET) scan, multiple series MRI sequences (T1, T2, T2 Flair, (T2-weighted-Fluid-Attenuated Inversion Recovery), sequences with contrast, and the like) and a plurality of machine learning models, such as multiple neural networks. In some embodiments, the plurality of machine learning models includes at least one high-sensitivity network with at least one high-specificity network.

Each of the plurality of machine learning models is trained separately using different parameters, architectures, image sizes/resolutions, optimizers, and loss functions such that each of the plurality of machine learning models produced output distinct from the other machine learning models given the same input images. Final segmentation combines individual segmentation results inference by each machine learning model in order to produce a more reliable segmentation than would be achieved using a single image modality and/or a single machine learning model.

Advantageously, an automated system for target and tissue segmentation will not only accelerate radiotherapy treatment planning process but also provide a more reliable target and organ contouring.

Although the present disclosure focuses on multi-imaging modalities and multi-machine learning models, those skilled in the art will understand that the system works with single model and single imaging modality.

Various embodiments of systems and methods for automated target and tissue segmentation using multi-modal imaging and ensemble machine learning models are provided below. In the following detailed description, numerous specific details are set forth to provide a thorough understanding of the claimed subject matter. However, it will be understood by those skilled in the art that claimed subject matter may be practiced without these specific details. Although the detailed description describes the present invention with example described for radiotherapy, it will be understood by those skilled in the art that the claimed subject matter may be used for general tumor and organ segmentation on medical images.

While the method and apparatus are described herein by way of example for several embodiments and illustrative drawings, those skilled in the art will recognize that the method and apparatus for automated target and tissue segmentation using multi-modal imaging and ensemble machine learning models is not limited to the embodiments or drawings described. It should be understood, that the drawings and detailed description thereto are not intended to limit embodiments to the particular form disclosed. Rather, the intention is to cover all modifications, equivalents and alternatives falling within the spirit and scope of the method and apparatus for automated target and tissue segmentation using multi-modal imaging and ensemble machine learning models defined by the appended claims.

Some portions of the detailed description which follow are presented in terms of operations on binary digital signals stored within a memory of a specific apparatus or special purpose computing device or platform. In the context of this particular specification, the term specific apparatus or the like includes a general purpose computer once it is programmed to perform particular functions pursuant to instructions from program software. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these or similar terms are to be associated with appropriate physical quantities and are merely convenient labels.

Unless specifically stated otherwise, as apparent from the following discussion, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

As used herein, the term "target" refers to an area requiring treatment, such as a tumor, while the term "organ" refers to any normal or healthy tissue not requiring treatment.

FIG. 1 illustrates a system 100 configured in accordance with one or more embodiments consistent with the present disclosure. FIG. 1 is a block diagram of a system 100 for analyzing images of a plurality of imaging modalities using ensemble machine learning models, according to one or more embodiments. A plurality of 2D and 3D (composites of 2D image slices) medical images 102 are input into the system 100. The medical images 102 are registered by processor 104 in order to align corresponding targets and organs across the different images 102. The memory 106 stores the aligned images. The segmentation processor 108 inputs the aligned images into each of a plurality of machine learning models, which each generate a score map comprising pixel values ranging, for example between 0 and 1, of the target and organs. The target image converter 110 applies a weight to the output from each of the machine learning models to prepare a final image segmentation result. The resulting image segmentation is displayed on display 112.

Figure 2:
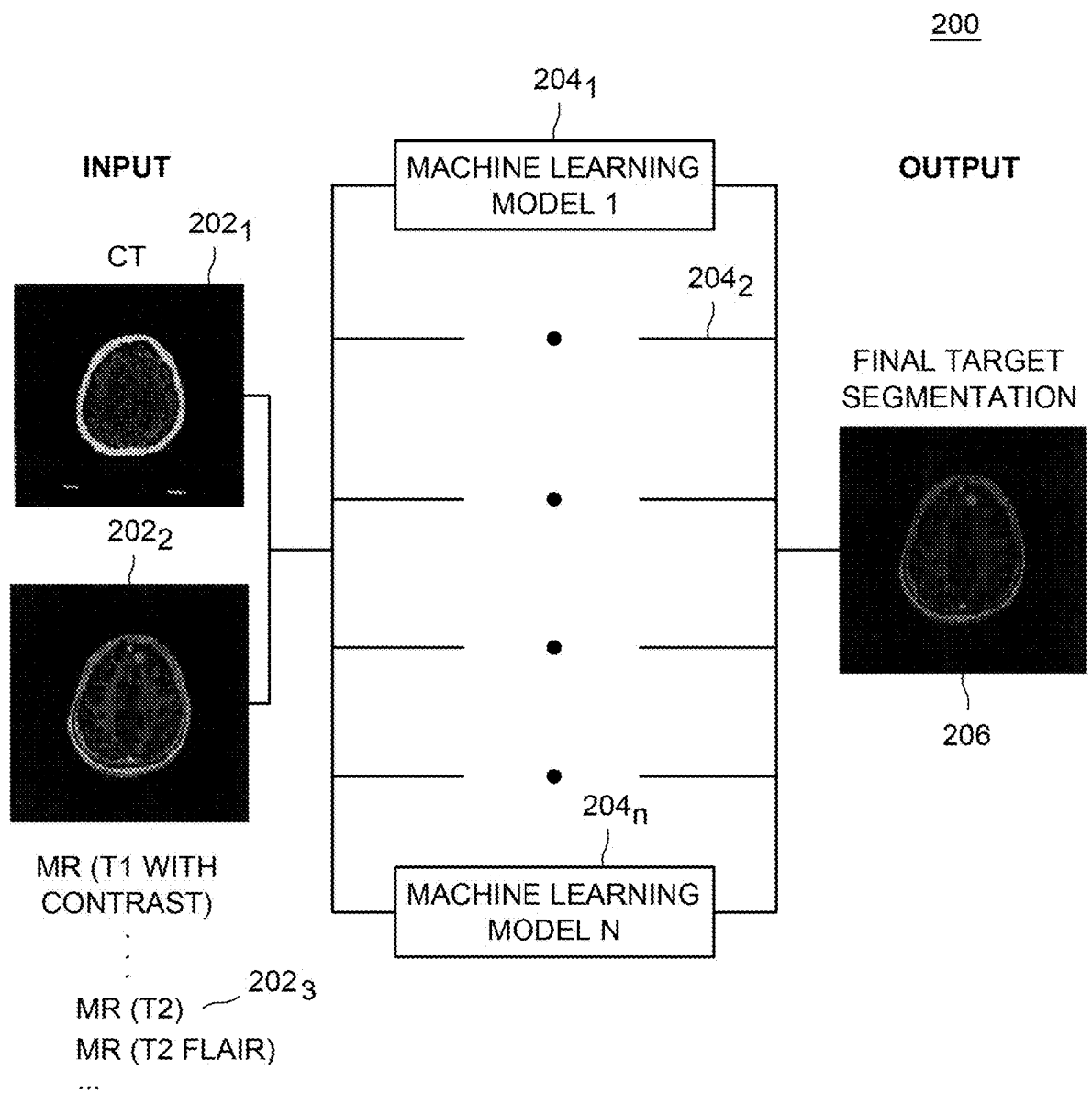
FIG. 2 depicts an exemplary embodiment of multi-modal imaging and ensemble machine learning models, according to one or more embodiments of the invention.

FIG. 2 depicts an exemplary embodiment of multi-modal imaging and ensemble machine learning models, according to one or more embodiments of the invention. A plurality of input imaging modalities $202_1$ $202_2$, . . . $202_n$ (collectively referred to as imaging modalities 202) are registered to align corresponding targets and organ across the different imaging modalities 202. The input imaging modalities may be, for example a CT scan $202_1$, an MRI (T1 with contrast) $202_2$, an MRI (T2) $202_3$, an MRI (T2 Flair) $202_4$. The aligned imaging modalities 202 are input into a plurality of machine learning models $204_1$ $204_2$, $204_3$, . . . $204_n$ (collectively referred to as machine learning models 204). Each machine learning model 204 is trained and optimized independently with different network architectures, parameters, image sizes/resolutions, optimizers, and loss functions such that each machine learning model 204 gives a distinct response.

During model training for multiple target and organ segmentation, the loss function may be designed to be related to the "volume" of the targets (organs). Specifically, a higher loss is assigned to smaller targets (organs), while a lower loss is assigned to larger targets, as large targets (organs) are generally easier to segment and detect. For example, the loss can be inverse proportional to the volume of targets (organs) or other functions related to volume or numbers of targets (organs) or numbers of types of targets (organs). This is beneficial to addressing smaller or more challenging targets (organs). Given input images, each of the machine learning models 204 generates segmentation of the target and organ independently, and the final segmentation 206 is a weighted sum of the segmentations from the machine learning models.

Each segmented target (tissue) is a group of connected components on the final segmentation. A final score is assigned to each segmented target (organ) using the average, or median, or linear/nonlinear combination of the score pixels (on $M_{Final}$) within the segmented range (a group of connected components), or score pixels combining other factors for example, tumor/organ size, locations, intensities, and the like and their linear/nonlinear combinations. Segmented targets and tissues are then sorted with their final scores. The system will show the top k most possible targets (tissues) with the final score for visualization. Users can choose k, or k can be pre-configured.

In addition to sorting segmented targets/tissues based on the final score, sorting can be based on segmented sizes, for example from large to small, small to large, and the like, or based on locations, for example from top to bottom, bottom to top, and the like.

The final segmentation of the target and organ 206 is output with a greater sensitivity and specificity than would be possible with a single image model and/or a single machine learning model. The final segmentation may be converted into various formats such as Digital Imaging and Communications in Medicine (dicom) standard, jpeg, and the like and may be loaded by medical imaging systems, such as Picture Archive and Communication System (PACS).

Figure 3:
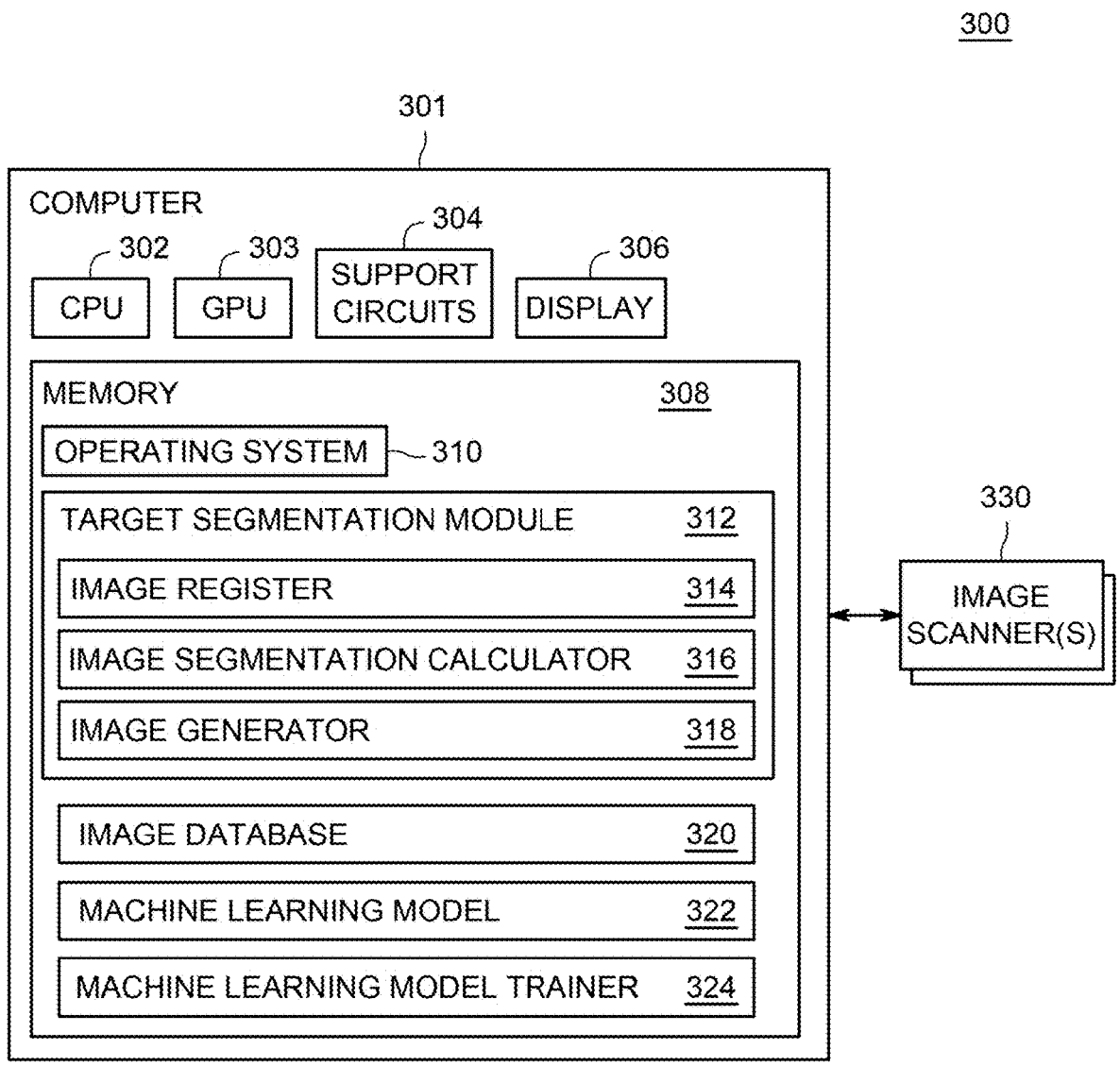
FIG. 3 depicts a block diagram of a system for automated target and tissue segmentation using multi-modal imaging and ensemble machine learning models, according to one or more embodiments.

FIG. 3 illustrates a system 300 configured in accordance with an embodiment of the present invention. FIG. 3 is a block diagram of a computer 301 for automated target and tissue segmentation using multi-modal imaging and ensemble machine learning models communicatively connected to a plurality of image scanners 330, according to one or more embodiments. The computer 301 is a computing device, for example a desktop computer, laptop, tablet computer, and the like. The computer 301 includes a Central Processing Unit (CPU) 302, Graphic Processing Units (GPUs) 303, support circuits 304, a display 306, and a memory 308. The CPU 302 may include one or more commercially available microprocessors or microcontrollers that facilitate data processing and storage. The various support circuits 304 facilitate the operation of the CPU 302 and include one or more clock circuits, power supplies, cache, input/output circuits, and the like. For machine learning model training and prediction (inference), processing using GPUs 303 is much faster than using the CPU 302. As such, CPU 302 is responsible for image pre-processing, such as image alignment, and post-processing, such as computing the weighted sum of segmentations from individual machine learning models, while GPUs 303 are responsible for all machine learning model processing.

The memory 308 includes at least one of Read Only Memory (ROM), Random Access Memory (RAM), disk drive storage, optical storage, removable storage and/or the like. In some embodiments, the display 306 is not integrated into the computer 300, but rather is communicatively couple, either wired, or wirelessly to the computer 300.

The memory 308 includes an operating system 310, a target segmentation module 312, an image database 320, a plurality of machine learning models 322, and a machine learning model trainer 324, the target segmentation module 312 includes an image register 314, an image segmentation calculator 316, and an image generator 318. The target segmentation module 312 comprises instructions executable by CPU 302 for receiving a plurality of images from the image scanners 330 and storing the received images in the image database 320. The image register 314 aligns the corresponding targets and organs across the plurality of images received by the target segmentation module 312.

The target segmentation module 312 inputs the aligned images into each of the plurality of machine learning models 322. Each of the plurality of machine learning models output a score map of pixels of the target and organs. The image segmentation calculator 316 using a weighting factor for each machine learning model to calculate a final map of the target and organs. The image generator 318 displays the final image segmentation result on display 306.

Each of the plurality of machine learning models 322 has been trained separately using machine learning model trainer 324 and GPUs 303. In some embodiments, convolutional machine learning models are used, where there are many neural layers connected to each other. The machine learning models might contain convolutional layers, max pooling layers, activation layers, dropout layers, etc., each of which contains some parameters and processes input signals from the previous layer and then sends the processed signals to the next layer. The input of the machine learning models is the medical images, while the output is tumor/tissue segmentation generated by the machine learning models. We calculate the difference between the output segmentation and the ground truth segmentation (generated by expert oncologists) using a defined loss function. The loss is then back-propagated (from output segmentation to input medical image) through each layer of the machine learning models. The parameters of each layer are then tuned (optimized) based on the back-propagated loss and selected optimizers. Typical optimizer methods are stochastic gradient descent and its variants such as Adam, RMSprop, etc.

To train the machine learning models, significant amounts of training data (pairs of medical images and the corresponding ground truth segmentations) are collected. Using the training data, we iterate the method described in the above paragraph (forward propagate the input signal, back-propagate the loss, tune the parameters of each neural layer based on the loss) many times such that the machine learning models can be optimized.

When training different machine learning models, different loss functions, optimizers, parameters, and combinations of neural layers are used. Also, the input images should be used with different resolution (sizes). For example, to train a high-sensitivity model, the input image can be cropped into small patches, each of which is sent to the model individually (such that the model can focus on small, detailed tumors), while to train a high-specificity model, the input image can be fed into the model as its original size (such that the model has a more comprehensive overview for the image).

The training data is collected and used to train the model periodically. For examples, the model may be trained using 1000 cases. The trained model is then used to predict target/tissue segmentation for future new cases. The prediction for the new case is herein referred to as 'model inference'. After for example a month, another 1000 new cases are collected for training (assuming oncologists also provide ground truth segmentation for the new cases), and then the model is trained again based on either the entire 2000 cases or the new 1000 cases only. Training/re-training the model periodically keeps our machine learning models updated.

Figure 4:
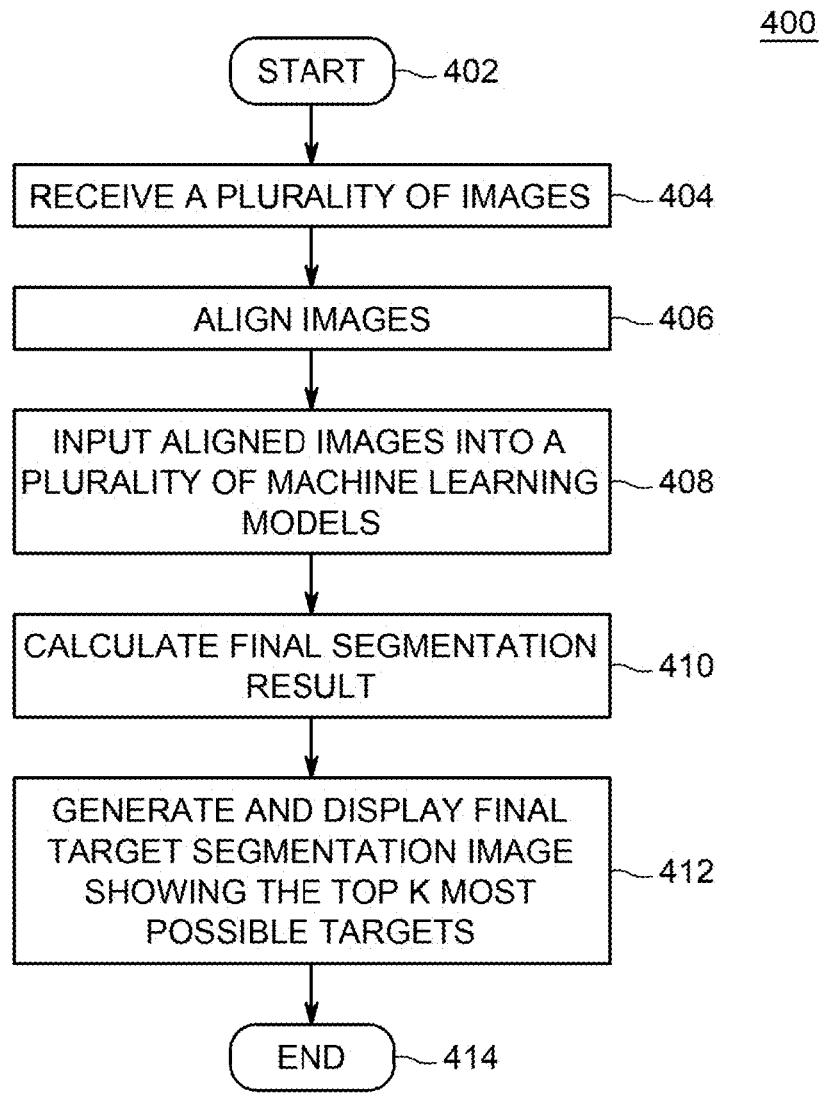
FIG. 4 depicts a flow diagram of a method for automated target and tissue segmentation using multi-modal imaging and ensemble machine learning models as performed by the system of FIG. 1, according to one or more embodiments.

FIG. 4 depicts a flow diagram of a method 400 for automated target and tissue segmentation using multi-modal imaging and ensemble machine learning models. Embodiments of the present disclosure are used to identify or discriminate between targets (e.g., tumors) and normal tissue and/or organs under investigation. In some embodiments, the material under investigation may be biological tissue where images constructed by differential intensity analysis are used for diagnostic and/or evaluation purposes.

The method 400 begins at step 402 and proceeds to step 404. At step 404, a plurality images of a plurality of image modalities are received (e.g., computer tomography (CT) scan, magnetic resonance imaging (MRI), positron emission tomography (PET) scan, multiple series MRI sequences (T1, T2, T2 Flair (T2-weighted-Fluid-Attenuated Inversion Recovery), sequences with contrast, and the like).

At step 406, the images from the plurality of image modalities are aligned. Each of the image modalities depicts a target. The target may be a tumor or area of focus. The images are combined such that targets and organs are aligned across the different imaging modalities. In some embodiments, the images from different modalities can be combined as a single "input" after registration (alignment).

The images may be combined by creating an additional dimension, named channel. For example, aligned CT images and MRI images have three dimensions (X,Y,Z), where X,Y,Z represent a number of pixels in the corresponding dimension. Then, the combined input becomes four dimensions (X,Y,Z,C), where C (means channel) equals to number of imaging modalities (2 in this example as we have CT and MRI).

In some embodiments, the images from the plurality of image modalities are not combined. Rather, segmentations are generated using each imaging modality only, such as CT input only and MRI input only separately, and the final segmentation is then combined as described below.

At step 408, the aligned images are used as input to a plurality of machine learning models. In some embodiments, the plurality of machine learning models includes at least one high-sensitivity (high true positive rate) network and at least one high-specificity (high true negative rate) network. Each machine learning model has been trained independently in order to optimize the machine learning model.

The aligned images are input into each machine learning model individually, such that each machine learning model provides a distinct output. The output generated by each machine learning model is a score map. The score map includes pixel values, for example between 0 and 1, of the target and organs.

At step 410, a final image segmentation result is calculated. Each machine learning model is given a weight. For example, each machine learning model (1-N) generates a map $M_1, M_2, \ldots, M_N$. Each machine learning model is given a weight a (between 0 and 1). The final image segmentation result is calculated using the following:

$$M_{Final} = \Sigma L_{k=1}^{N} \alpha_k M_k$$

A threshold may be applied to $M_{Final}$ to create a binary mask for the target or tissues so any value greater than the threshold is set to 1, while any value below the threshold is set to 1.

At step 412, the final image segmentation calculation is used to generate an image. The automated target and tissue segmentation using multi-modal imaging and ensemble machine learning models provides a reliable target and organ contouring. The segmented targets are then sorted with their final scores. The system displays the top k most possible targets with the final score for visualization. The value k may be input by a user, may be a pre-configured value, may be based on prior knowledge of a number of targets that should exist, or is an adjustable value, where the value can be adjusted using a scroll bar or other means on a graphical user interface. The method 400 ends a step 414.

Figure 5:
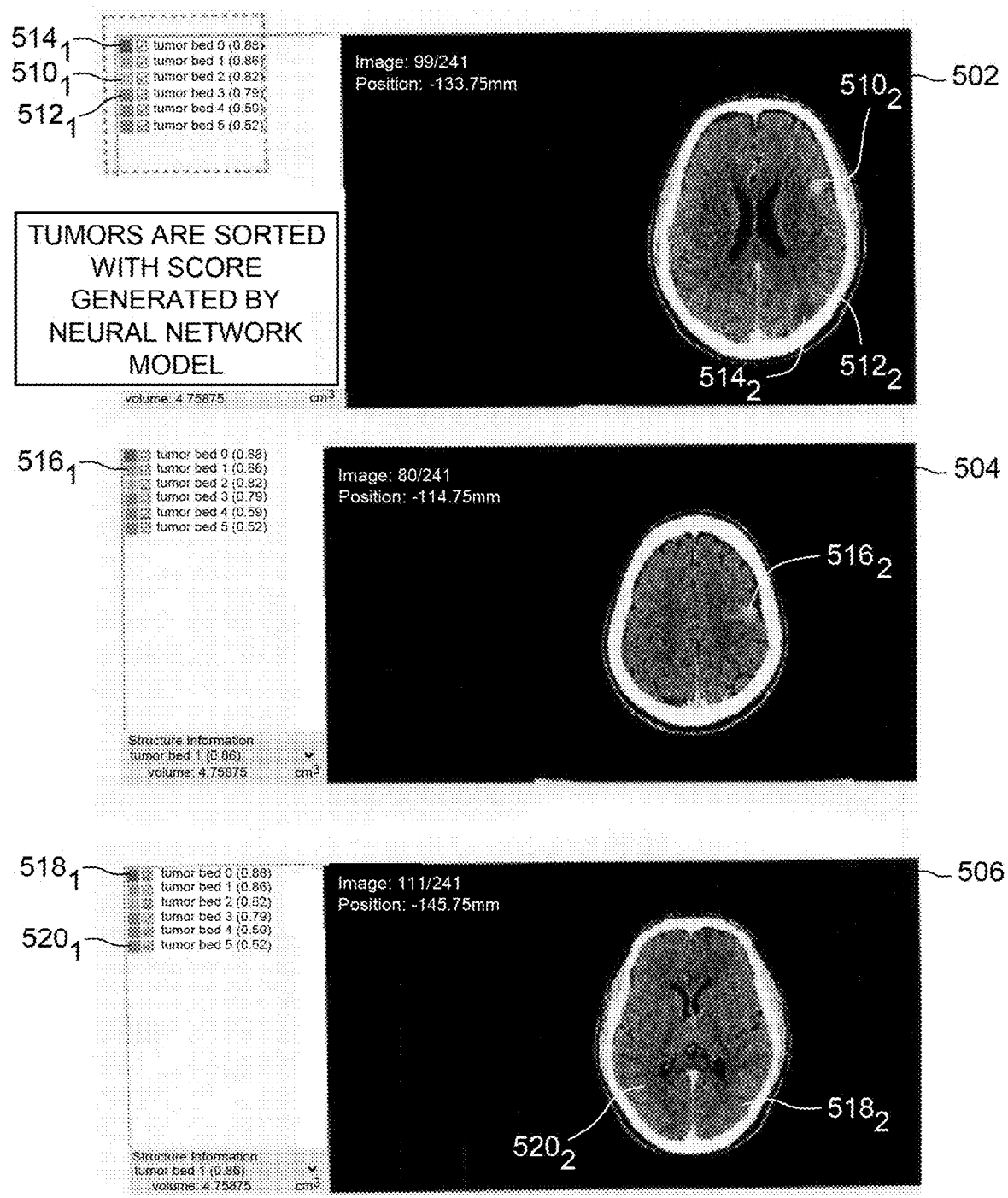
FIG. 5 depicts a display of the tumors sorted with scores generated by the machine learning model, according to one or more embodiments of the invention.

FIG. 5 depicts a display 500 of the exemplary tumor detection results 502, 504, and 506 sorted with scores generated by the machine learning model using the formula in step 410, according to one or more embodiments of the invention. During model inference, machine learning models (or other types of algorithms) generate a final score map ($M_{Final}$ ranging from 0 and 1) for each type of targets or organs. A threshold is then applied to the score map to create a binary mask ($M_{binary}$), so any value greater than the threshold is set to 1, while any value below the threshold is set to 0. Each segmented target (tissue) is a group of connected components on the binary mask. A final score is assigned to each segmented target (organ) using the average, or median, or linear/nonlinear combination of the score pixels (on m within the $M_{Final}$) segmented range (a group of connected components), or score pixels combining other factors for example, tumor/organ size, locations, intensities, and the like and their linear/nonlinear combinations. Segmented targets are then sorted with their final scores. The system shows the top k most possible targets (tissues) with the final score for visualization. A user may select a value for k, or k may be pre-configured. A plurality of examples is displayed in FIG. 5. Example 502 shows three tumors, specifically tumor $510_2$, $512_2$, and $514_2$, with scores displayed in the key at $510_1$, $512_1$, and $514_1$ respectively. Example 504 shows tumor $516_2$, with the score displayed in the key at $516_1$. Example 506 shows two tumors, specifically tumor $518_2$ and $520_2$, with scores displayed in the key at $518_1$ and $520_1$ respectively.

In addition to displaying the top-k predicted results to the users based on a fixed k and a threshold, our system is also able to show various top-k results based various values of k and the threshold entered by our users explicitly or implicitly [such as by specifying 1) prior knowledge of the number of tumors that should be detected, and/or 2) control of a scroll bar or the like to adjust the sensitivity or the specificity of the system, etc.]

Although top-k predicted results are displayed a whole for a given configuration (k, threshold, and other parameters), each predicted target (tissue) from the top-k results is presented in a way such that the user can individually edit or unselect.

Figure 6:
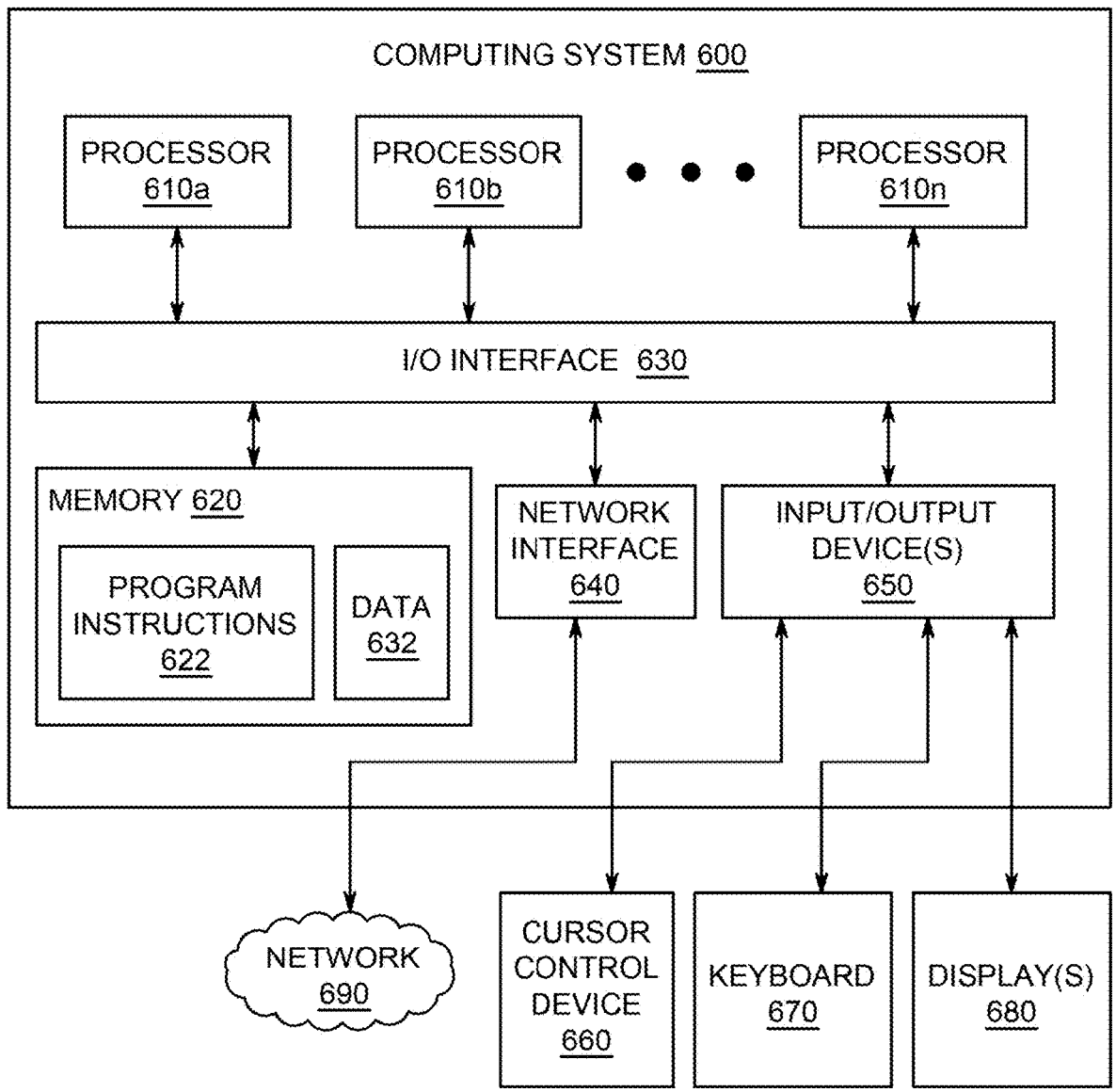
FIG. 6 is a detailed block diagram of a computer system for implementing, for example, the systems of FIG. 1 and/or FIG. 3, according to one or more embodiments.

FIG. 6 is a detailed block diagram of a computer system, according to one or more embodiments, that can be utilized in various embodiments of the present invention to implement the computer and/or the display devices, according to one or more embodiments.

Various embodiments of method and apparatus for automated target and tissue segmentation using multi-modal imaging and ensemble machine learning models, as described herein, may be executed on one or more computer systems, which may interact with various other devices. One such computer system is computer system 600 illustrated by FIG. 6, which may in various embodiments implement any of the elements or functionality illustrated in FIGS. 1-4. In various embodiments, computer system 600 may be configured to implement methods described above. The computer system 600 may be used to implement any other system, device, element, functionality or method of the above-described embodiments. In the illustrated embodiments, computer system 600 may be configured to implement method 400 (FIG. 4) as processor-executable executable program instructions 622 (e.g., program instructions executable by processor(s) 610) in various embodiments.

In the illustrated embodiment, computer system 600 includes one or more processors 610a-610n coupled to a system memory 620 via an input/output (I/O) interface 630. Computer system 600 further includes a network interface 640 coupled to I/O interface 630, and one or more input/output devices 650, such as cursor control device 660, keyboard 670, and display(s) 680. In various embodiments, any of the components may be utilized by the system to receive user input described above. In various embodiments, a user interface may be generated and displayed on display 680. In some cases, it is contemplated that embodiments may be implemented using a single instance of computer system 600, while in other embodiments multiple such systems, or multiple nodes making up computer system 600, may be configured to host different portions or instances of various embodiments. For example, in one embodiment some elements may be implemented via one or more nodes of computer system 600 that are distinct from those nodes implementing other elements. In another example, multiple nodes may implement computer system 600 in a distributed manner.

In different embodiments, computer system 600 may be any of various types of devices, including, but not limited to, a personal computer system, desktop computer, laptop, notebook, or netbook computer, mainframe computer system, handheld computer, workstation, network computer, a set top box, a mobile device such as a smartphone or PDA, a consumer device, video game console, handheld video game device, application server, storage device, a peripheral device such as a switch, modem, router, or in general any type of computing or electronic device.

In various embodiments, computer system 600 may be a uniprocessor system including one processor 610, or a multiprocessor system including several processors 610 (e.g., two, four, eight, or another suitable number). Processors 610 may be any suitable processor capable of executing instructions. For example, in various embodiments processors 610 may be general-purpose or embedded processors implementing any of a variety of instruction set architectures (ISAs). In multiprocessor systems, each of processors 610 may commonly, but not necessarily, implement the same ISA.

System memory 620 may be configured to store program instructions 622 and/or data 632 accessible by processor 610. In various embodiments, system memory 620 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing any of the elements of the embodiments described above may be stored within system memory 620. In other embodiments, program instructions and/or data may be received, sent or stored upon different types of computer-accessible media or on similar media separate from system memory 620 or computer system 600.

In one embodiment, I/O interface 630 may be configured to coordinate I/O traffic between processor 610, system memory 620, and any peripheral devices in the device, including network interface 640 or other peripheral interfaces, such as input/output devices 650. In some embodiments, I/O interface 630 may perform any necessary protocol, timing or other data transformations to convert data signals from one component (e.g., system memory 620) into a format suitable for use by another component (e.g., processor 610). In some embodiments, I/O interface 630 may include support for devices attached through various types of peripheral buses, such as a variant of the Peripheral Component Interconnect (PCI) bus standard or the Universal Serial Bus (USB) standard, for example. In some embodiments, the function of I/O interface 630 may be split into two or more separate components, such as a north bridge and a south bridge, for example. Also, in some embodiments some or all of the functionality of I/O interface 630, such as an interface to system memory 620, may be incorporated directly into processor 610.

Network interface 640 may be configured to allow data to be exchanged between computer system 600 and other devices attached to a network (e.g., network 690), such as one or more display devices (not shown), or one or more external systems or between nodes of computer system 600. In various embodiments, network 690 may include one or more networks including but not limited to Local Area Networks (LANs) (e.g., an Ethernet or corporate network), Wide Area Networks (WANs) (e.g., the Internet), wireless data networks, some other electronic data network, or some combination thereof. In various embodiments, network interface 640 may support communication via wired or wireless general data networks, such as any suitable type of Ethernet network, for example; via telecommunications/telephony networks such as analog voice networks or digital fiber communications networks; via storage area networks such as Fiber Channel SANs, or via any other suitable type of network and/or protocol.

Input/output devices 650 may, in some embodiments, include one or more communication terminals, keyboards, keypads, touchpads, scanning devices, voice or optical recognition devices, or any other devices suitable for entering or accessing data by one or more computer systems 600. Multiple input/output devices 650 may be present in computer system 600 or may be distributed on various nodes of computer system 600. In some embodiments, similar input/output devices may be separate from computer system 600 and may interact with one or more nodes of computer system 600 through a wired or wireless connection, such as over network interface 640.

In some embodiments, the illustrated computer system may implement any of the methods described above, such as the methods illustrated by the flowchart of FIG. 4. In other embodiments, different elements and data may be included.

Those skilled in the art will appreciate that computer system 600 is merely illustrative and is not intended to limit the scope of embodiments. In particular, the computer system and devices may include any combination of hardware or software that can perform the indicated functions of various embodiments, including computers, network devices, Internet appliances, PDAs, wireless phones, pagers, and the like. Computer system 600 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 600 may be transmitted to computer system 600 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium or via a communication medium. In general, a computer-accessible medium may include a storage medium or memory medium such as magnetic or optical media, e.g., disk or DVD/CD-ROM, volatile or non-volatile media such as RAM (e.g., SDRAM, DDR, RDRAM, SRAM, and the like), ROM, and the like.

The methods described herein may be implemented in software, hardware, or a combination thereof, in different embodiments. In addition, the order of methods may be changed, and various elements may be added, reordered, combined, omitted or otherwise modified. All examples described herein are presented in a non-limiting manner. Various modifications and changes may be made as would be obvious to a person skilled in the art having benefit of this disclosure. Realizations in accordance with embodiments have been described in the context of particular embodiments. These embodiments are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

While the foregoing is directed to embodiments of the present invention, other and further embodiments of the invention may be devised without departing from the basic scope thereof, and the scope thereof is determined by the claims that follow.

What is claimed is:

1. A computer-implemented method for automated target and tissue segmentation using at least one medical imaging modality and at least one machine learning model comprising:
    receiving at least one medical image modality, wherein at least one medical image of the at least one medical image modalities includes at least one target and/or at least one normal tissue or organ;
    inputting the at least one medical image into each of the at least one machine learning models;
    receiving, in response to the input, an output from each of the at least one machine learning models, wherein the outputs of the at least one machine learning models are combined when more than one output is received; and
    generating a final segmentation image including at least one segmented target and/or at least one normal tissue or organ based on the outputs of the at least one machine learning models,
    wherein the at least one machine learning model includes at least one of a high-sensitivity network or a high-specificity network.

2. The method of claim 1, wherein each of the at least one machine learning models is trained separately using different parameters, architectures, image sizes, image resolutions, optimizers, and loss functions.

3. A computer-implemented method, for automated target and tissue segmentation using at least one medical imaging modality and at least one machine learning model comprising:
    receiving at least one medical image modality, wherein at least one medical image of the at least one medical image modalities includes at least one target and/or at least one normal tissue or organ;
    inputting the at least one medical image into each of the at least one machine learning models;
    receiving, in response to the input, an output from each of the at least one machine learning models, wherein the outputs of the at least one machine learning models are combined when more than one output is received; and
    generating a final segmentation image including at least one segmented target and/or at least one normal tissue or organ based on the outputs of the at least one machine learning models,
    wherein each of the at least one machine learning models is trained separately using at least one different parameter, architecture, image size, image resolution, optimizer, or loss function, and
    wherein the loss function is related to a volume of a target, tissue and/or organ, wherein a higher loss is assigned to smaller targets, tissues and/or organs, and wherein a lower loss is assigned to larger targets, tissues and/or organs.

4. The method of claim 1, wherein each of the at least one machine learning model produces output distinct from the other machine learning models given the same input images.

5. The method of claim 1, wherein the output from each of the at least one machine learning models is a score map comprising pixel values ranging from 0 to 1.

6. The method of claim 1, further comprising applying a weight to the output from each of the at least one machine learning models before generating a final segmentation result.

7. The method of claim 6, further comprising:
    displaying the final segmentation result, wherein a final score is assigned to each segmented target and/or at least one normal tissue or organ using a linear/nonlinear combination of output score pixels within a segmented region generated from the at least one machine learning model, locations, sizes, and intensities of a segmented range.

8. The method of claim 7, further comprising displaying a number of most possible targets, tissues and/or organs with a final score for visualization, wherein the number is one of a value received from a user input, a pre-configured value, based on prior knowledge of a number of targets, tissues and/or organs that exist, or an value adjustable via a graphical user interface, wherein the graphical user interface comprises a scroll bar to adjust a sensitivity and/or specificity of the visualization, and, wherein each displayed target, tissue and/or organ is selectable and editable.

9. A system for automated target and tissue segmentation using at least one imaging modality and at least one machine learning models comprising:
    a) at least one processor;
    b) at least one input device; and
    c) at least one storage device storing processor-executable instructions which, when executed by the at least one processor, perform a method including:
    receiving at least one medical image modality, wherein at least one medical image of the at least one medical image modalities includes at least one target and/or at least one normal tissue or organ;
    inputting the at least one medical image into each of the at least one machine learning models;
    receiving, in response to the input, an output from each of the at least one machine learning models, wherein the outputs of the at least one machine learning models are combined when more than one output is received; and generating a final segmentation image including at least one segmented target and/or at least one normal tissue or organ based on the outputs of the at least one machine learning models,
wherein the at least one machine learning model includes at least one of a high-sensitivity network or a high-specificity network.

10. The system of claim 9, wherein each of the at least one machine learning models is trained separately using different parameters, architectures, image sizes, image resolutions, optimizers, and loss functions.

11. The system of claim 10, wherein the loss function is related to a volume of a target, tissue and/or organ, wherein a higher loss is assigned to smaller targets, tissues and/or organs and lower loss is assigned to larger targets, tissues and/or organs.

12. The system of claim 9, wherein each of the at least one machine learning model produces output distinct from the other machine learning models given the same input images.

13. The system of claim 9, wherein the output from each of the at least one machine learning models is a score map comprising pixel values ranging from 0 to 1.

14. The system of claim 9, further comprising applying a weight to the output from each of the at least one machine learning models before generating a final segmentation result.

15. The system of claim 14, further comprising:
displaying the final segmentation result, wherein a final score is assigned to each segmented target and/or at least one normal tissue or organ using a linear/nonlinear combination of output score pixels within a segmented region generated from the at least one machine learning model, locations, sizes, and intensities of a segmented range.

16. The system of claim 15, further comprising:
displaying a number of most possible targets, tissues and/or organs with a final score for visualization, wherein the number is one of a value received from a user input, a pre-configured value, based on prior knowledge of a number of target, tissue and/or organ that exist, or an value adjustable via a graphical user interface, wherein the graphical user interface comprises a scroll bar to adjust a sensitivity and/or specificity of the visualization, and, wherein each displayed target, tissue and/or organ is selectable and editable.

17. The method of claim 1, further comprising:
assigning a score to each of the at least one segmented target and/or at least one normal tissue or organ; and
sorting the at least one segmented target and/or at least one normal tissue or organ based on the scores.

18. The system of claim 9, the method further comprising:
assigning a score to each of the at least one segmented target and/or at least one normal tissue or organ; and
sorting the at least one segmented target and/or at least one normal tissue or organ based on the scores.

19. The method of claim 1, wherein the high-sensitivity network produces a high true positive rate, and the high-specificity network produces a high true negative rate.

* * * * *